United States Patent
Yukimasa et al.

(10) Patent No.: US 7,632,392 B2
(45) Date of Patent: Dec. 15, 2009

(54) SENSOR OF PYROPHOSPHATE AND SNP TYPING SENSOR USING THE SAME

(75) Inventors: Tetsuo Yukimasa, Kanagawa (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 83 days.

(21) Appl. No.: 12/112,249

(22) Filed: Apr. 30, 2008

(65) Prior Publication Data

US 2008/0293128 A1    Nov. 27, 2008

Related U.S. Application Data

(63) Continuation of application No. PCT/JP2007/050679, filed on Jan. 18, 2007.

(30) Foreign Application Priority Data

Jan. 23, 2006    (JP) .............. 2006-013368

(51) Int. Cl.
*G01N 27/416* (2006.01)
*G01N 27/327* (2006.01)

(52) U.S. Cl. .............. 205/777.5; 204/403.03; 204/403.14; 435/6

(58) Field of Classification Search ............ 204/403.01, 204/403.03, 403.14; 205/777.5, 792; 435/6
See application file for complete search history.

(56) References Cited

U.S. PATENT DOCUMENTS 5,658,443 A    8/1997 Yamamoto et al.

7,267,986 B2 *  9/2007 Yukimasa et al. ............. 436/34

FOREIGN PATENT DOCUMENTS

| JP | 61-012300 | 1/1986 |
|----|-----------|--------|
| JP | 03-054447 | 3/1991 |
| JP | 07-083872 | 3/1995 |
| JP | 2002-369698 | 12/2002 |
| JP | 2005-292022 | 10/2005 |
| WO | WO 03/078655 A1 | 9/2003 |

* cited by examiner

*Primary Examiner*—Kaj K Olsen
(74) *Attorney, Agent, or Firm*—McDermott Will & Emery LLP (57) ABSTRACT

A sensor of pyrophosphate which can detect pyrophosphate conveniently with high sensitivity in a method for measuring pyrophosphate in SNP typing utilizing a primer extension reaction is provided.

A sensor of pyrophosphate which is characterized by including: an insulative substrate 1; an electrode system that is formed thereon and has a measurement electrode 2 and a counter electrode 3; and a plurality of reaction reagent layers that are provided on the substrate 1 and include pyrophosphatase, glyceraldehyde-3-phosphate dehydrogenase, diaphorase, glyceraldehyde-3-phosphate, oxidized nicotineamide adenine dinucleotide, an electronic mediator, a magnesium salt and a buffer component, reaction reagent layer 36 including the enzyme being separated from reaction reagent layer 35 including the buffer component, and reaction reagent layer 37 including glyceraldehyde-3-phosphate being separated from the reaction reagent layer 35 including the buffer component.

18 Claims, 4 Drawing Sheets

SENSOR OF PYROPHOSPHATE AND SNP TYPING SENSOR USING THE SAME

This is a continuation application under U.S.C 111(a) of pending prior International application No. PCT/JP2007/050679, filed on Jan. 18, 2007, which in turn claims the benefit of Japanese Application No. 2006-13368 filed on Jan. 23, 2006, the disclosures of which Application are incorporated by reference herein.

BACKGROUND OF THE INVENTION

1. Field of the Invention

The present invention relates to a sensor for measuring pyrophosphate in a sample solution conveniently with high sensitivity, and a SNP typing sensor using the same.

2. Background of the Related Art

Pyrophosphate has been known to be prominently involved in intracellular enzymatic reactions. For example, in the process of protein synthesis, pyrophosphate is produced in a reaction to form aminoacyl tRNA from an amino acid via aminoacyl adenylate. In addition, for example, in the process of starch synthesis found in plants and the like, pyrophosphate is produced when ADP-glucose is produced by a reaction of glucose-1-phosphate and ATP. In addition thereto, pyrophosphate has been known to be involved in a variety of enzymatic reactions. Therefore, techniques for quantitatively detecting pyrophosphate are important in analyses of cellular states, the aforementioned enzymatic reactions and the like.

Known conventional methods for measuring pyrophosphate include a chemical method of Grindley et al., (see, Nonpatent Document 1: G. B. Grindley and C. A. Nichel, Anal. Biochem., Vol. 33. p 114 (1970)). However, this method is not preferred since concentrated sulfuric acid is used.

In Patent Document 1 (Japanese Patent Provisional Publication No. S61-12300), three kinds of methods for measuring pyrophosphate are disclosed in which an enzyme is utilized without using a chemical such as concentrated sulfuric acid. Those methods are explained in the following.

In the first method, pyruvate orthophosphate dikinase is allowed to act on pyrophosphate in the presence of phosphoenol pyruvate and adenosine monophosphate. Since pyruvic acid is produced by this reaction, the amount of pyrophosphate can be determined by measuring the amount of pyruvic acid. As the method for measuring the amount of pyruvic acid, two kinds of methods were proposed. One is a method in which when a catalytic action of lactate dehydrogenase is utilized to reduce pyruvic acid with NADH, decrease of NADH is colorimetrically determined. Another is a method in which pyruvate oxidase is allowed to act on the produced pyruvic acid, and generated hydrogen peroxide is lead to a dye to execute colorimetric determination.

In the second method, glycerol-3-phosphate cytidyl transferase is allowed to act on pyrophosphate in the presence of cytidine diphosphate glycerol. Glycerol triphosphate is produced by this reaction. Therefore, by measuring the amount of produced glycerol triphosphate, the amount of pyrophosphate can be determined. As the method for measuring the amount of glycerol triphosphate, two kinds of methods were proposed. One is a method in which when a catalytic action of glycerol-3-phosphate dehydrogenase is utilized to oxidize glycerol triphosphate with $NAD(P)^+$, increase of $NAD(P)H$ is colorimetrically determined. Another is a method in which glycerol-3-phosphate oxidase is allowed to act on the produced glycerol triphosphate, and generated hydrogen peroxide is lead to a dye to execute colorimetric determination of the same.

In the third method, ribitol-5-phosphate cytidyl transferase is allowed to act on pyrophosphate in the presence of cytidine diphosphate ribitol. Since this reaction produces D-ribitol-5-phosphate, measurement of the production amount enables the amount of pyrophosphate to be measured. As the method for measuring D-ribitol-5-phosphate, a method in which ribitol-5-phosphate dehydrogenase is allowed to act in the presence of $NAD^+$ (or $NADP^+$), and increase of NADH (or NADPH) is colorimetrically determined was proposed.

In addition, Patent Document 2 (Japanese Patent Provisional Publication No. 2002-369698) discloses a method in which: pyrophosphate is hydrolyzed into phosphoric acid by pyrophosphatase; thereafter the phosphoric acid is allowed to react with inosine or xanthosine by purine nucleoside phosphorylase; the generated hypoxanthine is oxidized into xanthine by xanthine oxidase, followed by additional oxidization to produce uric acid; and coloring is permitted by a coloring agent using peroxidase for the hydrogen peroxide generated in the oxidation process by xanthine oxidase.

However, since the absorbance or coloring of the sample is measured in these methods for measuring pyrophosphate, use of a comparatively large-scale apparatus including an optical system is required.

Meanwhile, an extension reaction of a nucleic acid is also one of important biological reactions in which pyrophosphate is involved.

In recent years, techniques in connection with genetic information have been extensively developed. In medical field, analyses of a disease-related gene have enabled therapy of the disease at a molecular level. Also, gene diagnoses have enabled tailor-made medicine for every individual patient. In the field of pharmaceutical, genetic information is used to specify protein molecules such as antibodies and hormones, which are utilized as a chemical. Also in the field of agriculture and foods, products have been produced utilizing a lot of genetic information.

Among such genetic information, gene polymorphism is particularly important. As our facial appearances and body figures vary from one another, genetic information of every person also varies in significant parts. Among the differences of the gene information, those exhibiting alteration of the base sequence at a frequency of no less than 1% of the population are referred to as gene polymorphism. Such gene polymorphism has been suggested to be involved in not only facial configuration of each of the individuals, but also causes of a variety of genetic diseases, as well as constitution, pharmaceutical preparation responsiveness, side effects by pharmaceutical preparations, and the like. Currently, relationships between the gene polymorphisms and diseases and the like have been investigated rapidly.

Among these gene polymorphisms, SNP (Single Nucleotide Polymorphism) has particularly attracted attention in recent years. The SNP refers to gene polymorphism including only one different base in the base sequence of genetic information. SNP has been reported to be present within human genomic DNA as many as two to three million, and expected for utilization in clinical field since it can be readily utilized as a marker of gene polymorphism. At present, for the techniques relating to SNP, in addition to researches of identification of the position of a SNP in a genome, and to relationship between SNP and a disease, developments of SNP typing techniques for discriminating the base at a SNP site have been executed.

There are a variety of types of techniques for SNP typing such as those in which hybridization is utilized, those in which a restriction enzyme is utilized, those in which an enzyme such as ligase is utilized, and the like. Among those techniques, the most convenient technique utilizes a primer extension reaction. In this technique, the SNP typing is carried out by determining the occurrence of a primer extension reaction.

For detection in a SNP typing technique in which a primer extension reaction is used, a method including detecting an actual DNA amplification product using a fluorescent dye and a method including using an immobilization probe, as well as a method including detecting pyrophosphate that is a byproduct of nucleic acid synthesis by DNA polymerase have been also proposed. In such methods, pyrophosphate produced along with progress of the primer extension reaction is converted into ATP for detecting the difference of progress of the extension reaction, and thereafter the amount of pyrophosphate is measured utilizing a luciferase reaction (see, Non-patent Document 2: J. Immunological Method, 156, 55-60, 1992).

Furthermore, Patent Document 3 (Pamphlet of International Patent Publication No. 03/078655) discloses a method in which a target nucleic acid in a sample solution is determined with high sensitivity by measuring pyrophosphate, and a method for conveniently typing a SNP. In Patent Document 3, there is disclosed a method for typing of a SNP sequence of a DNA including: subjecting the sample to a reaction system that includes DNA polymerase, deoxynucleotides, and a DNA probe having a SNP site and having a sequence complementary to a SNP sequence of a DNA; extending the DNA probe by a PCR (Polymerase Chain Reaction) reaction; converting pyrophosphatase produced with the extension of the DNA probe into an inorganic phosphoric acid by pyrophosphatase; and finally measuring the value of an electric current with an electrode using a measurement system that includes glyceraldehyde-3-phosphate, oxidized nicotineamide adenine dinucleotide, glyceraldehyde-3-phosphate dehydrogenase, diaphorase and potassium ferricyanide as an electronic mediator. According to this method, it is mentioned that the SNP sequence can be discriminated within 100 sec after adding the sample including pyrophosphate into the measurement system.

Since the measurement of pyrophosphate and the SNP typing are enabled by electrochemically determining the redox reaction of the electronic mediator in this method, it is disclosed as a method that is highly sensitive and convenient, without need of an optical system.

In such measurement of pyrophosphate and SNP typing, down sizing of the sensor chip is enabled by carrying necessary reagents in a dried state on the sensor substrate, and further, the measurement by a very simple operation can be performed.

Patent Document 4 (Japanese Patent Provisional Publication No. Hei 7-83872) discloses that when a buffer component and an enzyme are concomitantly carried on a biosensor of the reagent-carrying type in a dried state, deterioration of the enzyme activity can be prevented by separately arranging each of them.

SUMMARY OF THE INVENTION

However, according to the aforementioned measurement of pyrophosphatase, and SNP typing using the same, problems of failing in achieving stable characteristics are involved by merely arranging the buffer component and the enzyme separately so as to be carried in the dried state since much more reagents are used.

The present invention was made in order to solve the aforementioned problems, and an object of the invention is to provide a sensor for detecting pyrophosphate in a sample solution conveniently with high sensitivity, and a SNP typing sensor using the same.

In order to accomplish the object described above, the present invention has the following constitution. More specifically, an aspect of the present invention provides a sensor of pyrophosphate which is characterized by including: an insulative substrate; an electrode system that is formed on the insulative substrate and has at least a measurement electrode and a counter electrode; and a plurality of reaction reagent layers that are provided on the substrate and include pyrophosphatase, glyceraldehyde-3-phosphate dehydrogenase, diaphorase, glyceraldehyde-3-phosphate, oxidized nicotineamide adenine dinucleotide, an electronic mediator, a magnesium salt and a buffer component, the reaction reagent layer including the enzyme being separated from the reaction reagent layer including the buffer component, and the reaction reagent layer including the glyceraldehyde-3-phosphate being separated from the reaction reagent layer including the buffer component.

In another aspect, the present invention is further characterized in that the reaction reagent layer including the glyceraldehyde-3-phosphate is separated from the reaction reagent layer including the enzyme.

In another aspect, the present invention is further characterized in that the reaction reagent layer including the oxidized nicotineamide adenine dinucleotide is separated from the reaction reagent layer including the enzyme, the reaction reagent layer including the buffer component, and the reaction reagent layer including the glyceraldehyde-3-phosphate.

In another aspect, the present invention is further characterized in that the reaction reagent layers are formed on the insulative substrate at separated parts, respectively.

In another aspect, the present invention is further characterized in that the reaction reagent layers are formed on the insulative substrate by being laminated at the same part.

In another aspect, the present invention is further characterized in that the reaction reagent layers are formed on the measurement electrode by being laminated.

Still another aspect of the present invention provides a SNP typing sensor which is characterized by including: an insulative substrate; an electrode system that is formed on the insulative substrate and has at least a measurement electrode and a counter electrode; a measuring cavity provided on the substrate so as to surround the electrode system; a reaction cavity provided on the substrate; a flow path that connects the measuring cavity with the reaction cavity; and a plurality of reaction reagent layers that are provided on the substrate and include pyrophosphatase, glyceraldehyde-3-phosphate dehydrogenase, diaphorase, glyceraldehyde-3-phosphate, oxidized nicotineamide adenine dinucleotide, an electronic mediator, a magnesium salt and a buffer component within the measuring cavity, the reaction reagent layer including the enzyme being separated from the reaction reagent layer including the buffer component, and the reaction reagent layer including the glyceraldehyde-3-phosphate being separated from the reaction reagent layer including the buffer component.

In yet another aspect, the present invention is further characterized in that the reaction reagent layer including the glyceraldehyde-3-phosphate is separated from the reaction reagent layer including the enzyme.

In yet another aspect, the present invention is further characterized in that the reaction reagent layer including the oxidized nicotineamide adenine dinucleotide is separated from the reaction reagent layer including the enzyme, the reaction reagent layer including the buffer component, and the reaction reagent layer including the glyceraldehyde-3-phosphate.

In yet another aspect, the present invention is further characterized in that a DNA amplification reaction is performed in the reaction cavity.

In yet another aspect, the present invention is further characterized in that the DNA amplification reaction is a PCR reaction.

According to the present invention a sensor of pyrophosphate which is s sensor for measuring pyrophosphate in a sample solution conveniently with high sensitivity, and a SNP typing sensor using the same can be provided.

DETAILED DESCRIPTION OF THE PREFERRED EMBODIMENTS

Hereinafter, embodiments of the present invention will be explained with reference to drawings.

Embodiment 1

Figure 1:
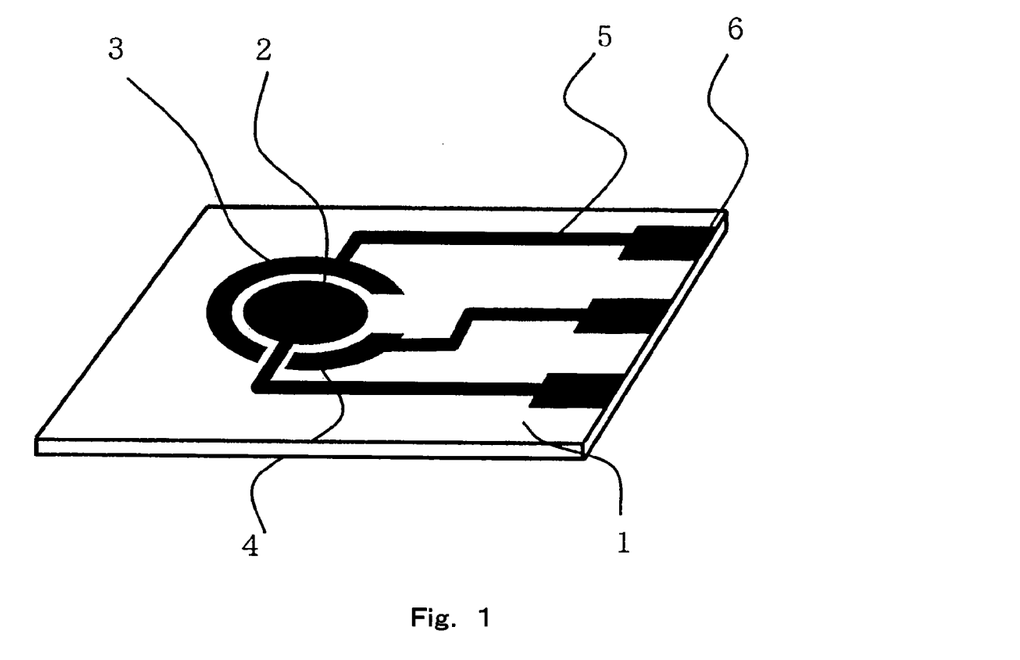
FIG. 1 shows a perspective view illustrating a structure of an electrode substrate according to one embodiment of the present invention.

FIG. 1 shows a perspective view illustrating an electrode substrate for demonstrating one embodiment of the present invention. On insulating substrate 1 are formed measurement electrode 2, counter electrode 3, and reference electrode 4. Although each electrode can be selected from noble metals such as gold, platinum and palladium, carbon and the like, gold is preferably selected as the electrode in light of the stability of the surface state.

As the reference electrode 4, a collating electrode that exhibits nonpolarity is more preferably used in light of stability of the electric potential in the solution, and furthermore, in light of convenience in handling, and the like, a silver/silver chloride electrode is preferably selected. Exemplary method for forming a silver/silver chloride electrode may be: a method including plating silver on a reference electrode 4 site of an electrode pattern formed with gold or platinum, and applying a voltage in an aqueous sodium chloride solution to silver chloridate the surface; a method in which the electrode body is constituted with a silver/silver chloride paste material; a method in which the surface of a silver paste is brought into contact with an aqueous solution of sodium hypochlorite; and the like.

Each electrode is electrically connected to terminal area 6 that is a connection area with the external circuit by electric conductive pattern 5. It is desired that the electric conductive pattern 5 and the terminal area 6 be also formed with a material similar to the electrode region, in light of the production step as well. As the method for forming the electrode and the electric conductive pattern on the insulating substrate 1, for example, printing of the electric conductive material on the insulating substrate 1, sputtering or vapor deposition of the electric conductive material followed by etching with photolithography or removing processing by a laser, direct sputtering of the electrode pattern using a mask, and the like may be suggested.

As the insulating substrate 1, a semiconductor such as silicon or germanium; glass such as quartz glass, lead glass or borosilicic acid glass, a ceramic, a resin, or the like may be selected. In light of the application as a disposable biosensor, a resin material is preferably selected taking into consideration the ease of processing and the aspect of cost.

The resin material may be selected from polycarbonate (PC), polystyrene (PS), polypropylene (PP), polyimide (PI), polytetrafluorinated ethylene (PTFE), polyphenylenesulfide (PPS), polyether ether ketone (PEEK), polyethylene terephthalate (PET), polymethyl methacrylate (PMMA), polyethylene-2,6-naphthalene (PEN), and the like. Among these, when a gold electrode is formed by sputtering, PET is preferably selected in light of adhesiveness with gold, and the like. Moreover, the insulating substrate 1 has a thickness of preferably 0.1 mm to 2.0 mm, and more preferably 0.188 mm to 1.0 mm, in light of ease of handling.

Figure 2:
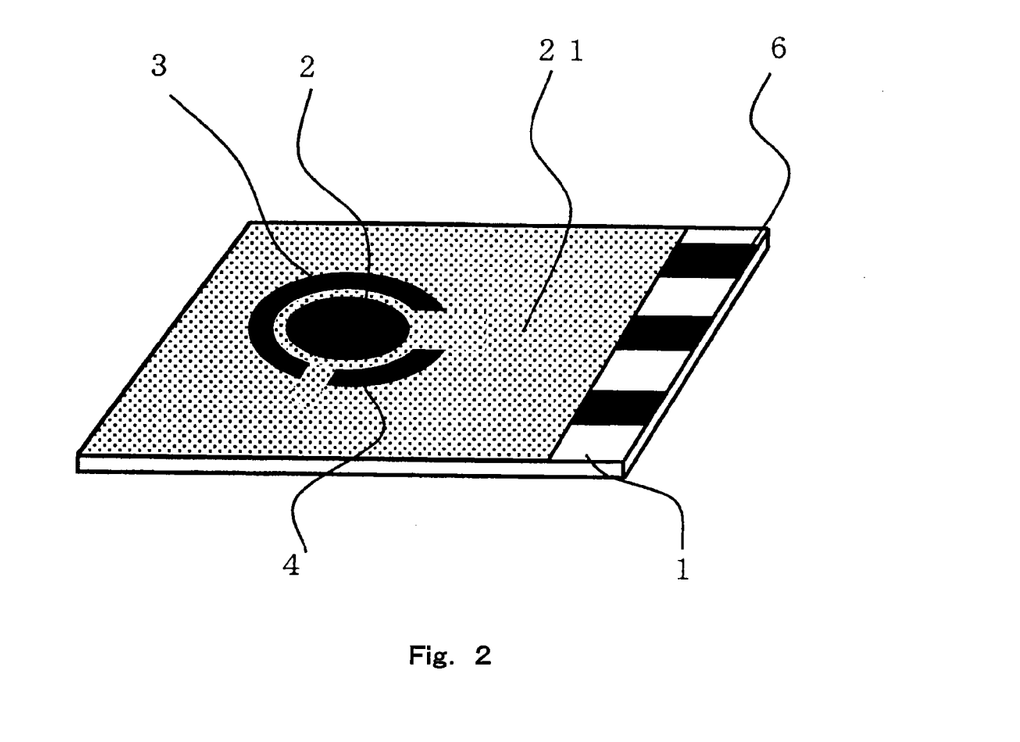
FIG. 2 shows a perspective view illustrating a structure of an electrode substrate according to one embodiment of the present invention.

Although the electrode substrate 7 can be directly used, in light of definition of the area of the electrode region, and the insulation and protection of the electric conductive pattern 5, it may be coated with an insulating film 21, as shown in FIG. 2. For the insulating film 21, a method in which a film of a resin material such as, for example, polyimide is formed by spin coating, followed by allowing the electrode region alone to be exposed with photolithography, a method in which an adhesive sheet punched out beforehand is attached on the electrode region, a method in which an insulative paste material is printed, or the like can be employed.

Whether or not the insulating film 21 is present, the electrode substrate 7 can be used even directly as a sensor of pyrophosphate by carrying the reagent, however housing may be also provided as demonstrated in the following for the purpose of preventing the measurement solution from drying and contamination.

Figure 3:
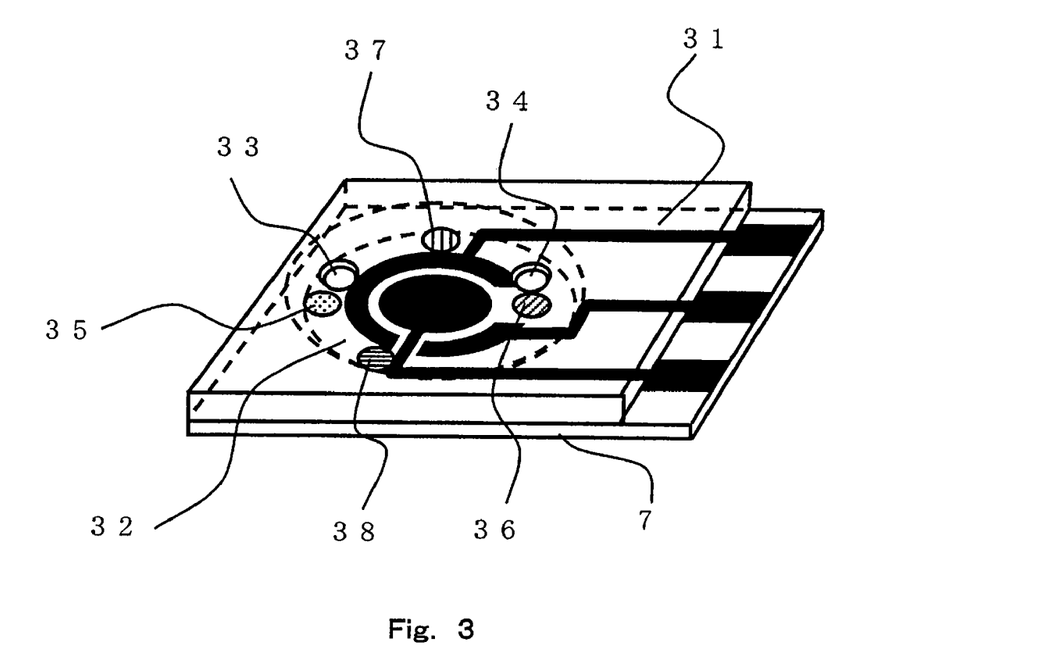
FIG. 3 shows a perspective view illustrating a structure of a housing substrate according to one embodiment of the present invention.
Figure 4:
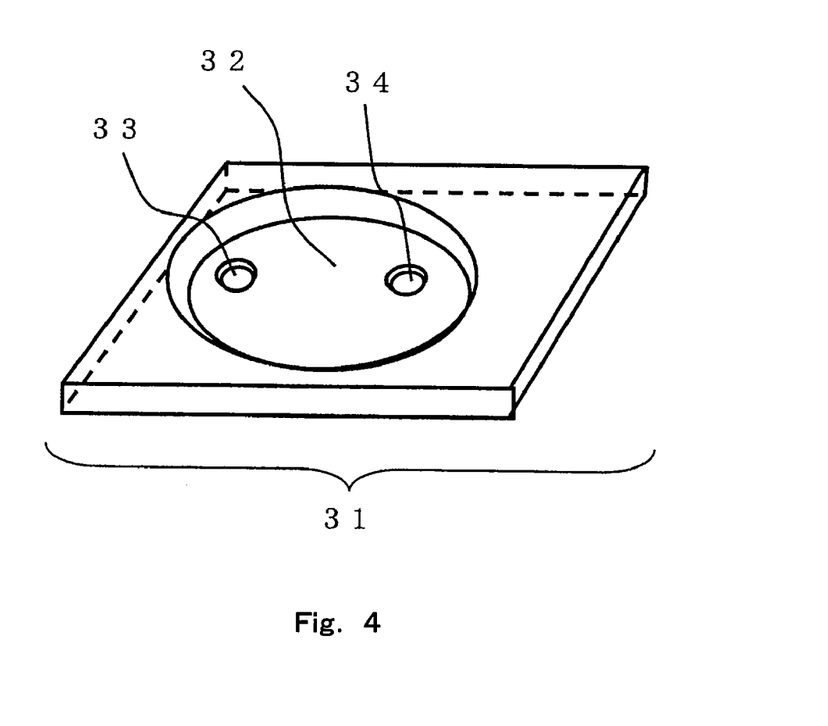
FIG. 4 shows a perspective view illustrating a structure of a sensor of pyrophosphate according to one embodiment of the present invention.

FIG. 3 shows a perspective view of the sensor of pyrophosphate illustrating one embodiment of the present invention, and this sensor has an electrode substrate shown in FIG. 1, and a housing substrate shown in FIG. 4. For the housing substrate 31 used in the biosensor according to the present invention, selection of a material which does not react with the sample solution is necessary, and a semiconductor such as silicon or germanium; glass such as quartz glass, lead glass or borosilicic acid glass, a ceramic, a resin, or the like can be selected. In light of the application as a disposable biosensor, a resin material is preferably selected taking into consideration the ease of processing and the aspect of cost, similarly to the insulating substrate 1.

The resin material may be selected from polycarbonate (PC), polystyrene (PS), polypropylene (PP), polyimide (PI), polytetrafluorinated ethylene (PTFE), polyphenylenesulfide (PPS), polyether ether ketone (PEEK), polyethylene terephthalate (PET), polymethyl methacrylate (PMMA), polyethylene-2,6-naphthalene (PEN), cyclic olefin copolymers (COC), polydimethyl siloxane (PDMS), and the like. PMMA and PC are particularly preferred since they have favorable transparency, whereby the state of the sample inside can be checked, and fine cutting processing is enabled. Also, when heat resistance is required, PC is particularly preferred.

As the method for forming cavity 32 on the housing substrate 31, when the housing substrate 31 is made of a resin material, cutting processing, as well as formation by a mold, emboss processing with thermal transfer or the like can be employed. Alternatively, the cavity 32 can be also formed by laminating sheets having a through hole.

The housing substrate 31 including the cavity 32 formed in such a manner is adhered with the electrode substrate 7; however, it is preferred that the housing substrate 31 and the electrode substrate 7 be completely adhered or stuck, whereby the sample in the cavity 32 is enclosed. For the adhesion, e.g., an adhesive such as an acrylic, epoxy based or silicone adhesive, an adhesive sheet such as a double-stick tape or the like can be used. Also, when a material having a low resistance to an organic solvent such as polycarbonate is used, adhesion can be effected by pouring an organic solvent such as chloroform to the interface between the housing substrate 31 and the electrode substrate 7, and pressurizing. Besides, when a thermoplastic resin such as PS or PMMA is used, a method by thermal fusion can be also employed.

The housing substrate 31 is provided with sample inlet 33 for injecting the sample into the cavity 32. Although at least one sample inlet 33 may be provided, it is preferred to provide air vent 34 as a hole for releasing the air, since the air vent 34 other than that used for injecting the sample serves as an escape route of the air inside the cavity 32, whereby the sample can be rapidly injected.

The positions of the inlet 33 and the air vent 34 are not particularly limited as long as they are connected to the cavity 32. The sample can be more rapidly introduced by subjecting the interior of the cavity 32 to a known hydrophilic treatment. After injecting the sample, the inlet 33 and the air vent 34 may be enclosed with a means such as an adhesive tape, but to employ in the open state is also acceptable in the case of the measurement for a short period of time.

First reaction reagent layer 35 containing a buffer component, an electronic mediator and a magnesium salt, second reaction reagent layer 36 containing pyrophosphatase, glyceraldehyde-3-phosphate dehydrogenase and diaphorase, third reaction reagent layer 37 containing glyceraldehyde-3-phosphate, and fourth reaction reagent layer 38 containing oxidized nicotineamide dinucleotide are carried in the cavity 32.

As is also understood from Examples described later, to divide into the four reaction reagent layers 35 to 38 is most preferred (see, sample D of Example) in terms of allowing a proportionality relation between the pyrophosphate concentration and the electric current to be exhibited, and increasing the slope of the proportionality relation to be greater.

Although the aforementioned slope may be decreased, the oxidized nicotineamide dinucleotide (fourth reaction reagent layer 38), and the buffer component, the electronic mediator and the magnesium salt (first reaction reagent layer 35) may be included in the identical reaction reagent layer (see, sample C of Example).

According to the present invention, at least the pyrophosphatase and the glyceraldehyde-3-phosphate dehydrogenase may be separated from the buffer component, and the glyceraldehyde-3-phosphate may be separated from the buffer component.

Therefore, similarly to the sample B of Example, not only the oxidized nicotineamide dinucleotide (fourth reaction reagent layer 38), and the buffer component, the electronic mediator and the magnesium salt (first reaction reagent layer 35) are included in the identical reaction reagent layer, but also the glyceraldehyde-3-phosphate (third reaction reagent layer 37), and the pyrophosphatase, the glyceraldehyde-3-phosphate dehydrogenase and the diaphorase (second reaction reagent layer 36) may be included in the identical reaction reagent layer. However, distinctness and the slope of the aforementioned proportionality relation are likely to be decreased.

The electronic mediator is desirably water soluble and stable in its oxidized form. For example, potassium ferricyanide can be used.

As the magnesium salt, one including a magnesium ion, being water soluble, and having a pH from neutral to weakly alkaline is acceptable, and, for example, magnesium chloride can be used.

In place of the oxidized nicotineamide dinucleotide ($NAD^+$), oxidized nicotineamide dinucleotide phosphate ($NADP^+$) may be also used. Also, oxidized nicotineamide dinucleotide phosphate ($NADP^+$) may be used together with the oxidized nicotineamide dinucleotide ($NAD^+$). The oxidized nicotineamide dinucleotide, oxidized nicotineamide dinucleotide phosphate, and any combination of these are referred to as "nucleotide" herein.

The position where the first reaction reagent layer 35, the second reaction reagent layer 36, the third reaction reagent layer 37, and the fourth reaction reagent layer 38 are carried may be an arbitrary place in the cavity 32, but the first reaction reagent layer 35, the second reaction reagent layer 36, the third reaction reagent layer 37, and the fourth reaction reagent layer 38 are carried at separate positions on the electrode substrate 7 as shown in FIG. 3.

The carrying of each of the reaction reagent layers 35 to 38 can be conducted by dropping each of the reagent solutions containing a given amount of the reagent, respectively, on predetermined places, followed by vacuum drying at an ordinary temperature, drying with hot air, freeze drying or the like to evaporate the solvent.

Embodiment 2

Figure 5:
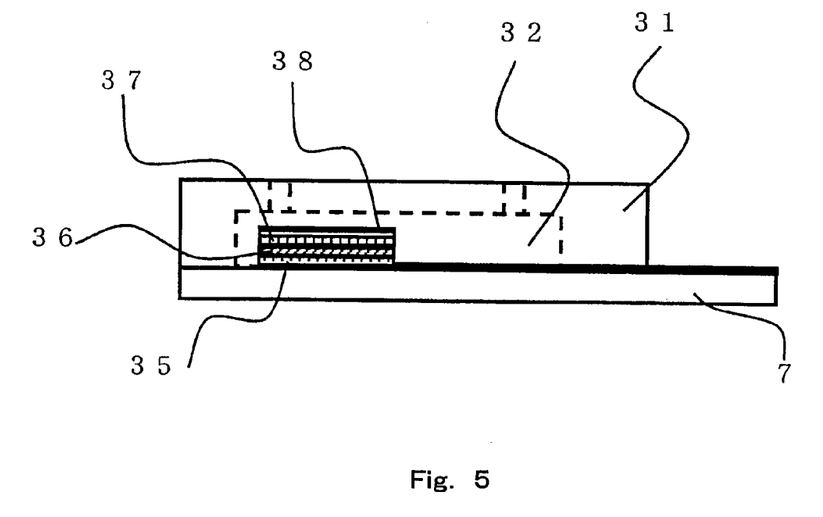
FIG. 5 shows a cross sectional view illustrating a structure of a sensor of pyrophosphate according to one embodiment of the present invention.

FIG. 5 shows a cross sectional view of the sensor of pyrophosphate illustrating one embodiment of the present invention. As shown in FIG. 5, the first reaction reagent layer 35, the second reaction reagent layer 36, the third reaction reagent layer 37, and the fourth reaction reagent layer 38 are laminated to be carried on the electrode substrate 7. In this step, a known technique can be used so as not to allow the first reaction reagent layer 35, the second reaction reagent layer 36, the third reaction reagent layer 37, and the fourth reaction reagent layer 38 to be mixed. For example, the second reaction reagent layer 36 can be formed as a water soluble thin film by forming a mixed layer with a polymer material such as carboxymethyl cellulose (CMC) when the first reaction reagent layer is formed. Subsequently, a hydrophilic polymer film such as polyvinylpyrrolidone (PVP) is formed on the second reaction reagent layer 36. Next, when the fourth reaction reagent layer 38 is provided, the reagent is dissolved in a solvent such as toluene in which PVP is insoluble, and the solution is dropped, whereby the fourth reaction reagent layer 38 is formed without causing mixing with the component in the first reaction reagent layer. Also for the third reaction reagent layer 37 and the fourth reaction reagent layer 38, similar process may be repeated thereby capable of forming them without mixing of the components in each reaction reagent layer. Since the PVP film is water soluble, each of the reaction reagent layers 35 to 38 will be rapidly mixed by feeding the sample solution.

Although each of the reaction reagent layers 35 to 38 was carried on the electrode substrate 7 according to the embodiment shown in FIG. 3 and FIG. 5, they may be carried at any position as long as it is situated in the cavity 32. Alternatively, they may be carried on the cavity 32 side of the housing substrate 31.

Embodiment 3

Figure 6:
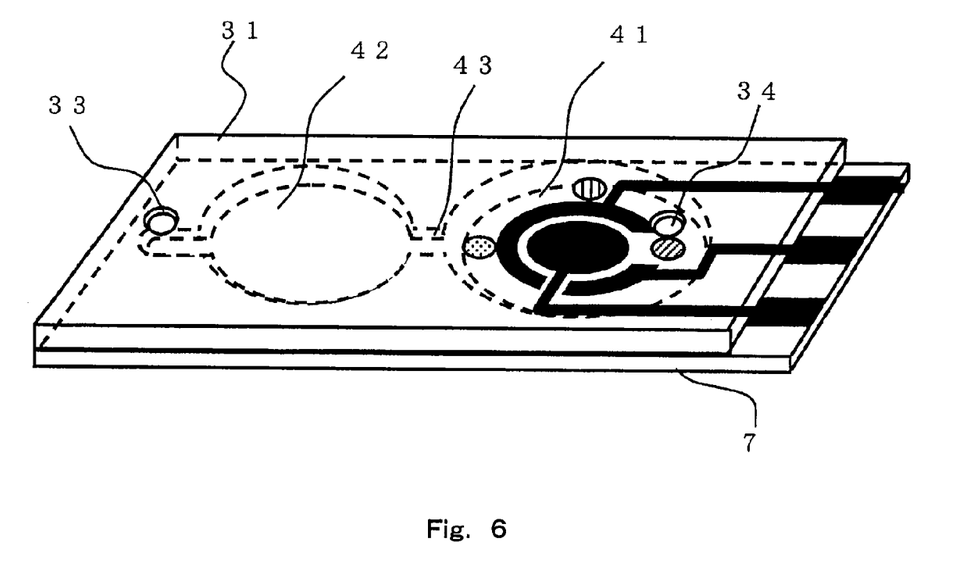
FIG. 6 shows a perspective view illustrating a structure of a SNP typing sensor according to one embodiment of the present invention.

FIG. 6 shows a perspective view of a SNP typing sensor illustrating one embodiment of the present invention. Similarly to FIG. 3, the sensor is constituted with electrode substrate 7 and housing substrate 31, however, the housing substrate 31 is provided with, in addition to the measuring cavity 41, PCR cavity 42, and flow path 43 for connecting the PCR cavity 42 with the measuring cavity 41. When the PCR reaction is carried out by injecting from the inlet 33, together with the DNA sample solution of a measurement target for the SNP typing, a reaction system that includes DNA polymerase, deoxynucleotides, and a DNA probe having a SNP site and having a sequence complementary to the SNP sequence of the DNA, followed by a temperature cycle at the PCR cavity 42 using a heater or the like, the DNA can be extended accompanied by production of pyrophosphate in the case in which the SNP site of the DNA of the measurement target for the SNP typing is complementary to the DNA prove having the SNP site. Meanwhile, in the case in which the SNP site of the DNA of measurement target for the SNP typing is non-complementary to the DNA prove having the SNP site, extension of the DNA probe is not caused, whereby no pyrophosphate is generated. Thereafter, pyrophosphate can be quantitatively determined depending on the SNP type when the sample solution following completion of the PCR reaction is allowed to move into the measuring cavity 41 via the flow path 43, thereby enabling the SNP typing of the DNA that is the measurement target. In addition, when a reaction system including DNA polymerase, deoxynucleotides, and a DNA probe having a SNP site and having a sequence complementary to the SNP sequence of the DNA is carried in the reaction cavity 42, the SNP typing of the DNA of the measurement target is enabled by injecting only the DNA sample solution of the SNP typing measurement target from the inlet 34.

Further, the means which can be used in allowing the sample solution to be moved from the reaction cavity 42 to the measuring cavity 41 via the flow path 43 may be any one of an external pump such as a syringe pump, a plunger pump or a peristaltic pump, a micro pump integrally incorporated on the biosensor, centrifugal force yielded by rotation of the biosensor itself, and the like.

EXAMPLES

Example 1

The biosensor of the present invention is explained in more detail below. However, the present invention is not limited by way of the following Examples.

Hereinafter, Examples in which pyrophosphate in a sample solution was measured using an electrode substrate according to one embodiment will be explained.

First, as the insulating substrate 1, a gold thin film having a thickness of 700 Å was formed by sputtering on a polyethylene terephthalate sheet having a thickness of 188 μm. Next, the measurement electrode 2, the counter electrode 3, the reference electrode 4, the electric conductive pattern 5 and the terminal 6 as shown in FIG. 1 were concomitantly formed by etching, and cut into a predetermined size to produce the electrode substrate 7. The area of the electrode of the measurement electrode 2 was 2.0 mm$^2$.

In addition, silver chloride paste (DB2275, manufactured by Acheson Japan Limited) was applied on the surface of the reference electrode 4 of the electrode substrate 7 produced as described above, and dried under a condition at 80° C. for 30 min to form a silver/silver chloride electrode on the surface of the reference electrode 4.

Next, the reagents for measurement were dried and carried. Each reagent was dropped on the electrode substrate 7 dividing into spots at 2 to 4 sites. The relationship between the reagent dropped on each spot, and the position of the spot is shown in Table 1.

TABLE 1

|  | A | B | C | D |
|---|---|---|---|---|
| Buffer | (1) | (1) | (1) | (1) |
| MgCl$_2$ | (1) | (1) | (1) | (1) |
| K$_3$Fe(CN)$_6$ | (1) | (1) | (1) | (1) |
| NAD$^+$ | (1) | (1) | (1) | (4) |
| GAP | (1) | (2) | (3) | (3) |
| PPase | (2) | (2) | (2) | (2) |
| GAPDH | (2) | (2) | (2) | (2) |
| DP | (2) | (2) | (2) | (2) |

Buffer: 1 M Tricine buffer (pH 8.0), 1 μl
MgCl$_2$: 10 mM Magnesium chloride, 3.2 μl
K$_3$Fe(CN)$_6$: 100 mM Potassium ferricyanide, 0.2 μl
NAD$^+$: 10 mM Oxidized nicotinamide adenine dinucleotide, 2 μl
GAP: 30 mM Glycerylaldehyde-3-phosphate, 0.7 μl
PPase: 200 U/ml Pyrophosphatase, 0.5 μl
GAPDH: 800 U/ml Glycerylaldehyde-3-phosphate dehydrogenase, 0.8 μl
DP: 1000 U/ml Diaphorase, 0.2 μl
(1) first reaction reagent layer 35
(2) second reaction reagent layer 36
(3) third reaction reagent layer 37
(4) fourth reaction reagent layer 38

Accordingly, the electrode substrate 7 on which the reagent spots were formed was left to stand still in a vacuum chamber, and vacuum dried at room temperature for 30 min. Thus, the sensors of pyrophosphate A to D were produced.

Then, as the sample solution, each 20 μl of 0 μM, 50 μM and 100 μM aqueous pyrophosphate solutions was added dropwise on each electrode substrate, followed by pipetting, and conducting incubation under a condition at 30° C. for 5 min. An electric potential of 600 mV with respect to the reference electrode 4 was applied to the measuring electrode 2, and the electric current yielded at the measuring electrode 2 upon this application was measured.

Figure 7:
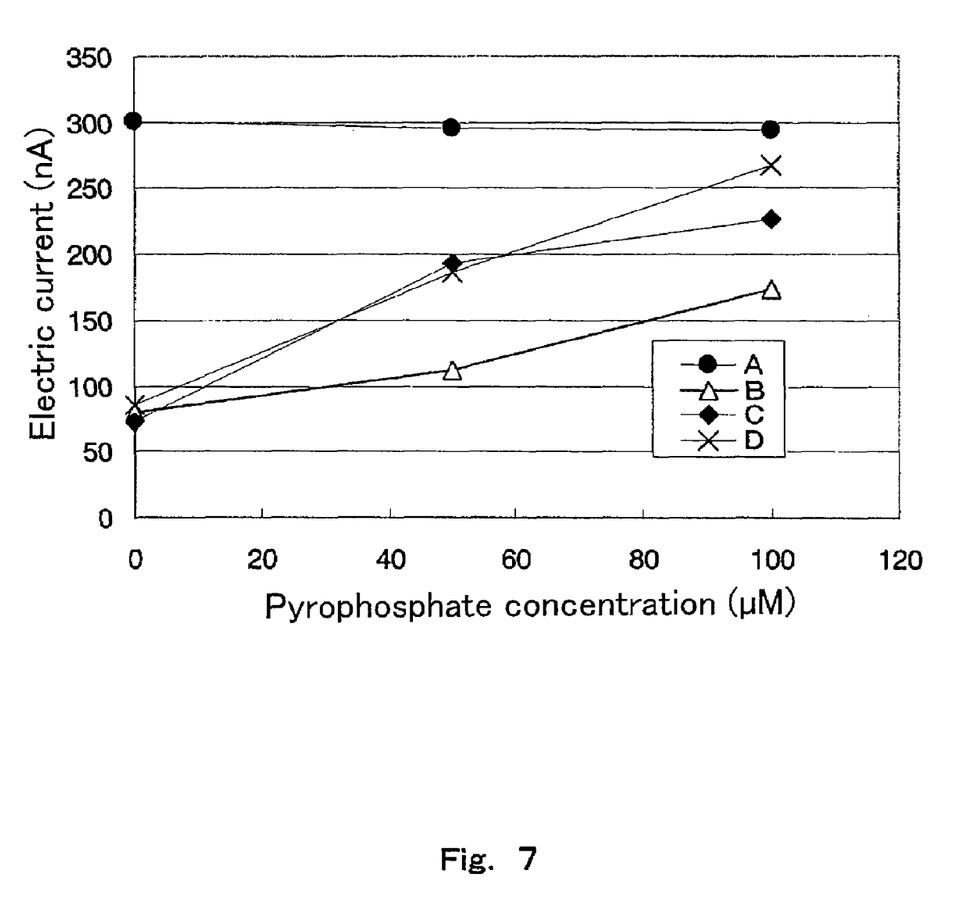
FIG. 7 shows a graph illustrating results according to one embodiment of the present invention.

Graphic representation of the electric current 60 sec after application of the electric potential at each pyrophosphate concentration is shown in FIG. 7.

For utilization as a sensor, of course, it is more preferred that the slope of each graph be greater, and the linearity be more superior.

According to the sensor A of pyrophosphate (2 spot) in which separation of the enzyme from other reagents was merely effected, high background was exhibited, and thus quantitative reliability was not achieved.

According to the sensor B of pyrophosphate (2 spot) in which GAP was dropped on the same spot as the enzyme, the electric current to meet with the pyrophosphate concentration was observed.

According to the sensor C of pyrophosphate (3 spot) in which GAP was provided as a single spot, the graph had a greater slope.

In addition, according to the sensor D of pyrophosphate (4 spot) in which NAD+ was provided as a single spot, a still greater slope could be exhibited, and the linearity was also increased.

Example 2

Example of SNP typing of a DNA in a sample solution carried out using the SNP typing sensor according to one embodiment is explained below.

First, a sensor G of pyrophosphate was produced similarly to Example 1.

However, as the housing substrate 31, one provided with in addition to the measuring cavity 41, the PCR cavity 42, and the flow path 43 for connecting the PCR cavity 42 with the measuring cavity 41 was used as shown in FIG. 6. The arrangement of the reaction reagent layers is identical with the sample C (3 spot type) of Example 1.

In an exemplary SNP typing model, Control Template (λDNA) (manufactured by Takara Shuzo Co., Ltd.) was used as a template; and Control Primer 1 (5'-GATGAGTTCGT-GTCCGTACAACT-3': SEQ ID NO: 1) and Primer 3 (5'-GGTTATCGAAATCAGCCACAGCGCC-3': SEQ ID NO: 2) of TaKaRa PCR Amplification Kit (manufactured by Takara Shuzo Co., Ltd.) as a completely matching primer, and Modified Primer 1' (5'-GATGAGTTCGTGTCCGTA-CAACA-3': SEQ ID NO: 3) and Primer 3 as a single base mismatch primer were used to perform the measurement (for amplification of 500 bp).

Using a sensor to which 12.4 µl of distilled water, 2.0 µl of 10×Z-Taq™ Buffer, 1.6 µl of 2.5 mM each dNTP Mixture, 0.8 µl of 25 µg/µl BSA, 0.2 µl of 2.5 U/µl TaKaRa Z-Taq™, each 1.0 µl of 20 pmol/µl Primer 1 and Primer 3, and 1.0 µl of 1 µg/ml λDNA were added (total volume: 20 µl) from the inlet 33 as SNP typing sensor X, and a sensor to which Primer 1' was added in place of Primer 1 as SNP typing sensor Y, PCR reactions were carried out under a condition of 30 cycles of at 98° C. for 1 sec, at 55° C. for 1 sec, and at 72° C. for 10 sec. The solution after completing the PCR reaction was fed from the PCR cavity 42 through the flow path 43 to the measuring cavity 41, and the measurement was performed similarly to Example 2. The results are shown in Table 2.

TABLE 2

|  | SNP typing sensor X | SNP typing sensor Y |
| --- | --- | --- |
| Electric current after 60 sec | 252 nA | 78 nA |

As is clear from Table 2, pyrophosphate produced as the PCR reaction proceeds which was caused at the PCR cavity 42 could be detected by electrochemical determination at the measuring cavity 41 with the SNP typing sensor X in which Primer 1 and Primer 3 were used as a primer which is completely complementary to the base sequence of λDNA that is a template. Meanwhile, according to the SNP typing sensor Y, since 3' end of Primer 1' is not complementary to the base sequence of λDNA that is a template, the extension reaction by Primer 3 with the template λDNA as a template was merely caused without proceeding of the amplification reaction by the PCR, whereby scarcely any electric current could be observed. Therefore, by using the SNP typing sensors X and Y, typing of the single base mismatch that is a SNP site model could be performed.

[Free Text of Sequence Listing]

<223> of SEQ ID NO: 1: primer

<223> of SEQ ID NO: 2: primer

<223> of SEQ ID NO: 3: primer

According to the present invention, a sensor of pyrophosphate which can detect pyrophosphate conveniently with high sensitivity in the method for measuring pyrophosphate by a process utilizing a primer extension reaction, and a SNP typing sensor can be provided.

The invention claimed is:

1. A sensor of pyrophosphate comprising
an insulative substrate, and
an electrode system that is formed on the insulative substrate and has at least a measurement electrode and a counter electrode, wherein:
pyrophosphatase, glyceraldehyde-3-phosphate dehydrogenase, diaphorase, glyceraldehyde-3-phosphate, a nucleotide, an electronic mediator, and a buffer component are carried on the substrate;
the pyrophosphatase is separated from the buffer component;
the glyceraldehyde-3-phosphate is separated from the buffer component;
the glyceraldehyde-3-phosphate dehydrogenase is separated from every one of the buffer component, the pyrophosphatase, and the glyceraldehyde-3-phosphate dehydrogenase; and
the nucleotide is oxidized nicotineamide adenine dinucleotide, oxidized nicotineamide adenine dinucleotide phosphate, or a combination thereof.

2. The sensor of pyrophosphate according to claim 1 wherein
the nucleotide is separated from every of the pyrophosphatase, the glyceraldehyde-3-phosphate dehydrogenase, the glyceraldehyde-3-phosphate, and the buffer component.

3. The sensor of pyrophosphate according to claim 1 which further comprises a first reaction reagent layer and a second reaction reagent layer, wherein
the first reaction reagent layer comprises the buffer component,
the second reaction reagent layer comprises the pyrophosphatase and the glyceraldehyde-3-phosphate dehydrogenase, and
the first reaction reagent layer is separated from the second reaction reagent layer when viewed from the direction along the normal line of the substrate.

4. The sensor of pyrophosphate according to claim 1 which further comprises a first reaction reagent layer and a second reaction reagent layer, wherein
the first reaction reagent layer comprises the buffer component,
the second reaction reagent layer comprises the pyrophosphatase and the glyceraldehyde-3-phosphate dehydrogenase, and
the first reaction reagent layer and the second reaction reagent layer are laminated when viewed from the direction along the normal line of the substrate.

5. The sensor of pyrophosphate according to claim 4 wherein
the first reaction reagent layer and the second reaction reagent layer are formed on the measurement electrode.

6. A SNP typing sensor comprising
an insulative substrate,
an electrode system that is formed on the insulative substrate and has at least a measurement electrode and a counter electrode,
a measuring cavity provided on the substrate so as to surround the electrode system,
a reaction cavity provided on the substrate, and
a flow path that connects the measuring cavity with the reaction cavity, wherein:
pyrophosphatase, glyceraldehyde-3-phosphate dehydrogenase, diaphorase, glyceraldehyde-3-phosphate, a nucleotide, an electronic mediator, and a buffer component are carried in the measuring cavity;
the pyrophosphatase is separated from the buffer component;
the glyceraldehyde-3-phosphate dehydrogenase is separated from the buffer component;
the glyceraldehyde-3-phosphate is separated from every one of the buffer component, the pyrophosphatase, and the glyceraldehyde-3-phosphate dehydrogenase; and
the nucleotide is oxidized nicotineamide adenine dinucleotide, oxidized nicotineamide adenine dinucleotide phosphate, or a combination thereof.

7. The SNP typing sensor according to claim 6 wherein
the nucleotide is separated from every of the pyrophosphatase, the glyceraldehyde-3-phosphate dehydrogenase, the glyceraldehyde-3-phosphate, and the buffer component.

8. The SNP typing sensor according to claim 6 wherein
a DNA amplification reaction is preformed in the reaction cavity.

9. The SNP typing sensor according to claim 8 wherein the DNA amplification reaction is a PCR reaction.

10. A method for determining pyrophosphate concentration in a sample solution with a sensor of pyrophosphate;
wherein the sensor comprises an insulative substrate and an electrode system that is formed on the substrate and has at least a measurement electrode and a counter electrode,
the substrate carries thereon pyrophosphatase, glyceraldehyde-3-phosphate dehydrogenase, diaphorase, glyceraldehyde-3-phosphate, nucleotide, an electronic mediator and a buffer component,
pyrophosphatase is separated from the buffer component,
glyceraldehyde-3-phosphate dehydrogenase is separated from the buffer component,
glyceraldehyde-3-phosphate is separated from any of the buffer component, pyrophosphatase and glyceraldehyde-3-phosphate dehydrogenase,
the nucleotide is selected from the group consisting of oxidized nicotineamide adenine dinucleotide, oxidized nicotineamide adenine dinucleotide phosphate or a combination thereof, and the method comprises the steps of:
(i) dropping the sample solution onto the substrate,
(ii) determining electric current value on the electrode system, and
(iii) quantitating pyrophosphate concentration in the sample solution from the electric current value.

11. The method according to claim 10, wherein said nucleotide is separated from any of pyrophosphatase, glyceraldehyde-3-phosphate dehydrogenase, glyceraldehyde-3-phosphate and the buffer component.

12. The method according to claim 10;
wherein said sensor further comprises a first reaction reagent layer and a second reaction reagent layer,
the first layer comprises a buffer component, the second layer comprises pyrophosphatase and glyceraldehyde-3-phosphate dehydrogenase, and
the first layer is separated from the second layer when viewed from the direction along the normal line of the substrate.

13. The method according to claim 10;
wherein said sensor further comprises a first reaction reagent layer and a second reaction reagent layer,
the first layer comprises a buffer component,
the second layer comprises pyrophosphatase and glyceraldehyde-3-phosphate dehydrogenase, and
the first layer and the second layer are laminated when viewed from the direction along the normal line of the substrate.

14. The method according to claim 13 wherein said first layer and said second layer are formed on said measurement electrode.

15. A method for identifying SNP type of DNA in a sample solution with an SNP typing sensor;
wherein the sensor comprises an insulative substrate, an electrode system that is formed on the substrate and has at least a measurement electrode and a counter electrode, a measuring cavity mounted on the substrate so as to surround the electrode system, a reaction cavity mounted on the substrate and a flow path that connects the measuring cavity to the reaction cavity,
the substrate carries therein pyrophosphatase, glyceraldehyde-3-phosphate dehydrogenase, diaphorase, glyceraldedhyde-3-phosphate, a nucleotide, an electronic mediator and a buffer component, pyrophosphatase is separated from the buffer component, glyceraldehyde-3-phosphate dehydrogenase is separated from the buffer component,
glyceraldehyde-3-phosphate is separated from any of the buffer component, pyrophosphatase and glyceraldehyde-3-phosphate dehydrogenase,
the nucleotide is selected from the group consisting of oxidized nicotineamide adenine dinucleotide, oxidized nicotineamide adenine dinucleotide phosphate or a combination thereof, and
the method comprises the steps of:
(I) injecting the sample solution into the reaction cavity,
(II) transferring the reaction solution to the reaction cavity through the flow path,
(III) determining electric current value in the electrode system, and
(IV) identifying SNP type of DNA in the sample solution based on the electric current value.

16. The method according to claim 15 wherein said nucleotide is separated from any of pyrophosphatase, glyceraldehyde-3-phosphate dehydrogenase, glyceraldehyde-3-phosphate and the buffer component.

17. The method according to claim 15 wherein DNA amplification reaction is performed in said reaction cavity.

18. The method according to claim 17 wherein said amplification reaction is PCR reaction.

* * * * *

UNITED STATES PATENT AND TRADEMARK OFFICE
CERTIFICATE OF CORRECTION

| | | |
|---|---|---|
| PATENT NO. | : 7,632,392 B2 | Page 1 of 1 |
| APPLICATION NO. | : 12/112249 | |
| DATED | : December 15, 2009 | |
| INVENTOR(S) | : Tetsuo Yukimasa et al. | |

It is certified that error appears in the above-identified patent and that said Letters Patent is hereby corrected as shown below:

ON THE TITLE PAGE:

In Item "(56) References Cited", below the data listed under "FOREIGN PATENT DOCUMENTS" change the following:

"WO WO03/078655 A1 9/2003" change to --WO 03/078655 A1 9/2003--

Signed and Sealed this

Fourteenth Day of December, 2010

David J. Kappos
*Director of the United States Patent and Trademark Office*

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial
<220> FEATURE:
<223> OTHER INFORMATION: Chemically Synthesized

<400> SEQUENCE: 1
gatgagttcg tgtccgtaca act                                    23

<210> SEQ ID NO 2
<211> LENGTH: 25
<212> TYPE: DNA
<213> ORGANISM: Artificial
<220> FEATURE:
<223> OTHER INFORMATION: Chemically synthesized

<400> SEQUENCE: 2
ggttatcgaa atcagccaca gcgcc                                  25
```

-continued

```
<210> SEQ ID NO 3
<211> LENGTH: 23
<212> TYPE: DNA
<213> ORGANISM: Artificial
<220> FEATURE:
<223> OTHER INFORMATION: Chemically synthesized

<400> SEQUENCE: 3
gatgagttcg tgtccgtaca aca                                              23
```